US010029959B2

(12) United States Patent
Stoyanova et al.

(10) Patent No.: US 10,029,959 B2
(45) Date of Patent: Jul. 24, 2018

(54) PROCESS FOR OBTAINING OLEFINS BY METATHESIS

(71) Applicant: Borealis AG, Vienna (AT)

(72) Inventors: Mariana Stoyanova, Berlin (DE); Evgeny Kondratenko, Rostock (DE); David Linke, Rostock (DE); Eberhard Ernst, Weissenfels (DE); Rene Dicke, Leonding (AT)

(73) Assignee: Borealis AG, Vienna (AT)

( * ) Notice: Subject to any disclaimer, the term of this patent is extended or adjusted under 35 U.S.C. 154(b) by 0 days.

(21) Appl. No.: 15/109,479

(22) PCT Filed: Dec. 30, 2014

(86) PCT No.: PCT/EP2014/079407
§ 371 (c)(1),
(2) Date: Jul. 1, 2016

(87) PCT Pub. No.: WO2015/101612
PCT Pub. Date: Jul. 9, 2015

(65) Prior Publication Data
US 2016/0347687 A1 Dec. 1, 2016

(30) Foreign Application Priority Data
Jan. 2, 2014 (EP) .................................. 14150042

(51) Int. Cl.
C07C 6/04 (2006.01)
B01J 37/04 (2006.01)
(Continued)

(52) U.S. Cl.
CPC ............ C07C 6/04 (2013.01); B01J 23/02 (2013.01); B01J 23/30 (2013.01); B01J 35/0006 (2013.01);
(Continued)

(58) Field of Classification Search
CPC ......................................................... C07C 6/04
See application file for complete search history.

(56) References Cited

U.S. PATENT DOCUMENTS 3,365,513 A  1/1968 Heckelsberg
3,546,313 A  12/1970 Banks
(Continued)

FOREIGN PATENT DOCUMENTS

DE   2137361 C3   2/1972
EP   1854776 A1   11/2007
(Continued)

OTHER PUBLICATIONS

Banks et al.; "New Developments and Concepts in Enhancing Activities of Heterogeneous Metathesis Catalysts"; Journal of Molecular Catalysis; 1985; pp. 117-131; vol. 28.
(Continued)

Primary Examiner — In Suk C Bullock
Assistant Examiner — Alyssa L Cepluch
(74) Attorney, Agent, or Firm — The Webb Law Firm

(57) ABSTRACT

The present invention relates to a process for obtaining an olefin by metathesis comprising feeding at least one stream comprising at least one olefin as starting material to at least one reactor comprising at least one main catalyst bed comprising a) at least one first catalyst component comprising a metathesis catalyst, and b) at least one second catalyst component comprising a catalyst for double bond isomerization, whereby the first and second catalyst are physically mixed with each other, wherein the at least one stream comprising at least one olefin as starting material is co-fed with hydrogen gas in a concentration range between 0.01 Vol % and 0.2 Vol % in respect to the total gas amount in the stream, and the metathesis process is conducted in the at
(Continued)

least one reactor at a pressure between 0.1 MPa and 3.0 MPa and at a temperature between 250° C. and 300° C.

21 Claims, 2 Drawing Sheets

(51) Int. Cl.
*C07C 5/25* (2006.01)
*B01J 35/00* (2006.01)
*B01J 23/02* (2006.01)
*B01J 23/30* (2006.01)
*B01J 35/02* (2006.01)

(52) U.S. Cl.
CPC .............. *B01J 37/04* (2013.01); *C07C 5/2512* (2013.01); *B01J 35/023* (2013.01); *C07C 2521/08* (2013.01); *C07C 2521/10* (2013.01); *C07C 2523/02* (2013.01); *C07C 2523/28* (2013.01); *C07C 2523/30* (2013.01); *Y02P 20/52* (2015.11)

(56) References Cited

U.S. PATENT DOCUMENTS

| | | | |
|---|---|---|---|
| 3,865,751 A | 2/1975 | Banks et al. | |
| 3,915,897 A | 10/1975 | Reusser et al. | |
| 4,547,617 A | 10/1985 | Welch | |
| 4,575,575 A | 3/1986 | Drake et al. | |
| 6,281,402 B1 | 8/2001 | Coupard et al. | |
| 7,525,007 B2 | 4/2009 | Sumner | |
| 7,977,522 B2 | 7/2011 | Takai et al. | |
| 8,013,200 B2 | 9/2011 | Takai et al. | |
| 8,440,874 B2 * | 5/2013 | Ramachandran | B01J 23/007 585/643 |
| 2010/0056839 A1 | 3/2010 | Ramachandran et al. | |
| 2010/0167911 A1 | 7/2010 | Shum | |

FOREIGN PATENT DOCUMENTS

| | | |
|---|---|---|
| EP | 2151424 A1 | 2/2010 |
| WO | 2005049534 A1 | 6/2005 |
| WO | 2010028267 A2 | 3/2010 |

OTHER PUBLICATIONS

Wu et al.; "The Effect of Hydrogen on the Carbonaceous Layer Formed on Molybdenum Model Catalysts during High Temperature Propylene Metathesis"; Journal of Catalysis; 1998; pp. 172-176; vol. 173.

* cited by examiner

PROCESS FOR OBTAINING OLEFINS BY METATHESIS

CROSS-REFERENCE TO RELATED APPLICATIONS

This application is the United States national phase of International Application No. PCT/EP2014/079407 filed Dec. 30, 2014, and claims priority to European Patent Application No. 14150042.1 filed Jan. 2, 2014, the disclosures of which are hereby incorporated in their entirety by reference.

BACKGROUND OF THE INVENTION

Field of the Invention

The present invention relates to a process for obtaining an olefin by metathesis.

Description of Related Art

Butenes are the $C_4H_8$ mono-olefin isomers such as 1-butene, cis-2-butene, trans-2-butene and iso-butene (2-methylpropene). If it is not specifically mentioned, cis-2-butene, trans-2-butene are also called as 2-butene within the frame of the present invention. The sum of cis-2-butene, trans-2-butene, and 1-butene is denoted as n-butenes. Butenes are almost always commercially produced as by-products in a petroleum refinery by cracking processes or by catalytic ethene dimerisation. Butenes can be used for multiple purposes like in the manufacture of polymers and other chemicals like insecticides, antioxidants, adhesives, sealants or elastomers.

The use of n-butenes for the production of propene has gained industrial importance in the last decades. The synthesis of propene using n-butenes as starting material is based on the metathesis reaction. Hereby, 2-butene is converted in the presence of ethene to propene according to the following overall reaction scheme:

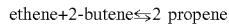

ethene+2-butene⇌2 propene

This reaction occurs typically in the presence of a catalyst comprising metal oxide of the group 6 or 7 of the periodic system of the elements (PSE). Typical active components of catalysts used for olefin metathesis are tungsten oxide supported on silica (U.S. Pat. No. 3,365,513) or rhenium oxides and molybdenum oxides supported on alumina or silica alumina (U.S. Pat. No. 4,547,617; U.S. Pat. No. 6,281,402).

Various modifications and improvements of the metathesis catalysts have been described. The physical mixing of the metathesis catalyst with an isomerisation catalyst for shifting the double bond in 1-butene to 2-butene has been proven to increase the overall production yield (U.S. Pat. No. 3,865,751; U.S. Pat. No. 3,915,897; U.S. Pat. No. 4,575,575). Typical double bond isomerisation catalysts include basic metal oxides as for instance magnesium oxide or calcium oxide. The use of magnesium oxide (MgO) as a co-catalyst enables the reduction of the reaction temperature to 250-300° C. from approximately 400° C. for pure silica supported tungsten oxide ($WO_3/SiO_2$). The weight ratio of MgO to $WO_3/SiO_2$ is in the range of 0.1-20. Magnesium oxide has the function to isomerise 1-butene to 2-butene since both olefins are present in technical feeds. It is important to highlight that magnesium oxide alone shows negligible metathesis activity.

Besides its ability to act as an isomerisation catalyst magnesium oxide has also been known for its ability to remove or destroy traces of contaminants from the olefin feed that are detrimental to metathesis catalysts, in particular when used as a "guard bed" (J. Mol. Cat. 1985, 28:117-131). Magnesium oxide can be for instance arranged on top of a composition comprising the metathesis catalyst and an isomerisation catalyst (US 2010/0056839 A1, US 2010/167911 A1). Here the optimal catalyst activation is combined with the guard pre-bed function to remove poisons and the isomerisation of 1-butene to 2-butene. When applying this approach a technical metathesis reactor is typically filled with a mixture of MgO and $WO_3/SiO_2$ as main bed and an MgO pre-bed upstream of the main bed.

Besides modifications of the catalyst system the metathesis process can also be influenced by adapting the olefin flow entering the synthesis reactor.

For instance, it has been reported (J. Cat. 173 (1998) 172-176) that when using pure molybdenum or pure molybdenum oxide catalysts for the propene metathesis (propene 4 ethene+2-butene) at 600° C. and reduced pressure, the addition of hydrogen to the reaction feed decreases the amount of carbon deposited on the surface and correspondingly increases the rate of the metathesis reaction, even though this reaction does not require hydrogen. This enhancing effect of hydrogen is ascribed to the removal of carbonaceous deposits from metathesis active sites and thus leading to an increase in the reaction rate of propene conversion. According to this article the coke content is build up very fast at the beginning of the reaction. It is noteworthy that the catalyst used in this previous study did not contain magnesium oxide as promoter.

Furthermore, the use of hydrogen for molybdenum/rhenium mixed catalysts has also been reported (DE 2137661 C3).

EP 1854 776 A1 describes that the metathesis reaction with a mixed catalyst bed can be carried out by co-feeding hydrogen with the gaseous olefin starting material stream. The initial purposes for addition of hydrogen to the olefin feed are i) the reduction of the reaction temperature down to 200° C., ii) the reduction of the amount of generated by-products and iii) the reduction of the catalyst sensibility towards butadiene. It was especially reported in this patent that the "durability of the catalyst activity" is increased by the application of hydrogen.

According to EP 1 854 776 A1 the amount of hydrogen gas added is in the range between 0.1 and 80 vol %, preferably 0.2 and 50 vol % of the total gas amount fed into the reactor. It is reported that if the amount of hydrogen is below the lower range limit no effect may be detectable and if the amount of hydrogen is above the upper range limit hydrogenation of olefins may be occur. Thus, a drawback of the hydrogen application is the formation of saturated hydrocarbons such as propane from the target olefin propene, since the metathesis catalyst also shows hydrogenation activity.

In another approach the superficial velocity (flow rate) in meter/seconds was set to 0.1 to 2 m/s for reducing the contact time of the gas stream with the catalyst (EP 2151 424 A1). The hydrogen concentration in the feed was also reduced to a range of 0.05 to 10 vol %, preferably to a range of 0.08 to 5 vol %. In this case the reaction temperature can be in a range between 100 and 500° C., preferably 130 and 350° C. and the applied pressure can be in a range between 0.01 and 20 MPa, preferably 0.05 and 10 MPa. Noteworthy is that according to the examples cited in EP 2151 424 A1 the hydrogen concentration tested is 1 vol % or 0.3 vol % at metathesis reaction condition of 300° C. and 3.5 MPa, respectively. In each case about 20% of the supplied hydrogen was consumed for non-desired hydrogenation of ethene and propene to ethane and propane, respectively. Thus, even at lowest hydrogen concentration of 0.3 Vol % tested in EP 2151 424 A1 a substantial and undesired hydrogenation of the olefins could not be avoided.

Commercial metathesis plants are not designed for the application of hydrogen co-feeds. Small amounts of light or lower hydrocarbons are removed in the frame of the deep temperature distillation of ethene. They are sent back to cracker. In case of co-feeding large amounts of hydrogen, enlarged hydrogen removal equipment is necessary that is connected with additional investment costs. In addition, operating with feeds containing high concentration of hydrogen does not make sense in metathesis plants, because hydrogen would reduce the feed concentration of 2-butene and/or ethene and also negatively influence the reaction rate and more importantly space-time yield (STY) of propene. Moreover, such operation would favor the enrichment of hydrogen in the recycling gas stream which increases the separation costs.

Therefore, it is desirable i) to limit the hydrogen concentration in the feed to small amounts and simultaneously ii) to increase initial Space-Time-Yield of propene. The latter requirement is very important from a commercial viewpoint, because ethene/2-butene cross-metathesis over MgO/$WO_3$—$SiO_2$ is characterized by an induction period (period of increasing propene production with rising time on stream) of several hours/days. Such activating behavior is difficult to understand when considering the known positive hydrogen impact on propene metathesis on molybdenum-containing catalysts as described in J. Cat. 173 (1998) 172-176. As mentioned in this article the coke formation is fast during the first hours on metathesis stream. Taking into account the deactivating impact of coke, it is difficult to explain why the activity of MgO/$WO_3$—$SiO_2$ passes over a maximum with reaction time. The butene feed also doesn't contain any detectable amounts of butadiene. Therefore, there must exist other origins governing for the metathesis catalyst system MgO/$WO_3$—$SiO_2$ compared to a pure molybdenum oxide catalyst.

It is therefore an object of this invention to provide a process which allows for an optimisation of the olefin, in particular propene, production by improving the initial space time yield of the process.

SUMMARY OF THE INVENTION

Accordingly, a process for obtaining an olefin by metathesis of other olefin(s) is provided, said process comprising feeding at least one stream comprising at least one olefin as starting material to at least one reactor comprising at least one main catalyst bed comprising a) at least one first catalyst component comprising a metathesis catalyst, and b) at least one second catalyst component comprising a catalyst for double bond isomerisation, whereby the first and second catalysts are physically mixed with each other.

The present process is characterized in that
the at least one stream comprising at least one olefin as starting material is co-fed with hydrogen in a concentration range between 0.01 vol % and 0.2 vol % with respect to the total gas amount in the stream, and
the metathesis process is conducted in the at least one reactor at a total pressure between 0.1 MPa and 3.0 MPa and at a temperature between 250° C. and 300° C.

Surprisingly it has been found that metathesis reaction can be carried out with a high initial activity (high initial space time yield), i.e. practically without any activation phase, and with a reduced deactivation rate of the catalyst if hydrogen is co-fed with the olefin stream in a concentration range between 0.01 vol % and 0.2 vol % at the claimed temperature and pressure conditions.

When using these specific reaction conditions for a metathesis reaction surprisingly no formation of hydrogenated paraffins such as propane or ethane is detectable. This means that the supplied hydrogen is not consumed for hydrogenation of fed or formed olefins. This is surprising and was not expected in view of the results reported in EP 2 151 424 A1. Only by choosing the specific parameters of the present process—i.e. very low hydrogen concentration, restricted temperature and low total pressure range—it is possible to conduct the metathesis process without side product formation but still with an increased initial space time yield of the desired olefin.

In a preferred embodiment of the present process the hydrogen gas is co-fed in a concentration range between 0.05 vol % and 0.15 vol %, preferably between 0.05 Vol % and 0.1 Vol % in respect to the total gas amount in the stream. The low hydrogen concentration in the gas stream enables an unexpected increase of the initial conversion rate and at the same time maintains the catalytic activity of the metathesis catalyst for an extended period of time.

Hydrogen can be mixed with the olefin stream immediately before entering the synthesis reactor. It is however also possible and conceivable that the hydrogen is fed to an evaporator and mixed there with the olefin stream. The gas stream mixed in the evaporator is subsequently fed into the metathesis reactor. Important is that the hydrogen and olefin stream are mixed before contacting the main catalyst bed. In an embodiment of the present method hydrogen is mixed to a standard olefin feed comprising olefin and nitrogen (for example a $C_2H_4$/trans-2-$C_4H_8$/$N_2$ flow) before entering the reactor. The added hydrogen replaces hereby a specific percentage of the nitrogen in the standard olefin feed.

In another embodiment of the present process the reaction pressure is between 0.12 MPa and 2.5 MPa, preferably between 0.5 MPa and 2.0 MPa, most preferably between 1.0 MPa and 2.0 MPa. A typical pressure range may be also between 2.0 and 3.0 MPa. Applying these specific pressure conditions the present metathesis process is conducted in the most efficient manner. In particular, when conducting the present process at a low total pressure a deactivation of the metathesis catalyst by the hydrogen in the gas stream is reduced or even completely avoided.

In a further embodiment the present process is conducted at reaction temperature between 270° C. and 300° C., preferably between 280° C. and 300° C. The specific temperature range is sufficient high for the olefin conversion by metathesis while at the same time—in particular in combination with the preferred hydrogen concentration and total pressure range—the undesired formation of side products is suppressed or reduced. Furthermore, the co-feeding of hydrogen prevents coke-formation on the active catalytic centres in the main catalyst bed; the overall productivity and selectivity of the metathesis reaction is increased.

It is furthermore preferred that at least two olefins are fed as starting material. Hereby one of the at least two olefins used as starting material comprises at least two carbon atoms (C2-compound), in particular ethene, and the second of the at least two olefins used as starting material comprises at least four carbon atoms (C4-compound), in particular 2-butene.

The at least two olefins may be supplied to the reaction reactor as a mixed stream or in form of separated streams. When using 2-butene as starting material, the butene component may be supplied as cis- or trans-2-butene or mixtures thereof. A technical 2-butene stream may contain additional small amounts of n-butane, iso-butane, iso-butene, 1-butene. In some embodiments the mixed C4 stream is pre-treated to increase the 2-butene content in the feed for the metathesis reaction. If a crude C4 cut from an e.g. naphtha cracker is used compounds like 1,3-butadiene, allenes or acetylenes have to be removed by a selective hydrogenation step.

The olefin mixture is then contacted with the catalyst bed, whereby isomerisation in particular of 1-butene to 2-butene and the synthesis of propene from ethene and 2-butene by metathesis occur.

In a further preferred embodiment of the present process the ratio of the C2-compound and the C4-compound is 20:1, preferably 10:1, more preferably 4:1, and most preferably 2.5:1. Thus, preferably an excess of the two carbon olefin is used. Higher C2/C4 ratios are preferred for suppressing side reactions.

In a further embodiment the metathesis catalyst of the main catalyst bed comprises metal oxides from metals of group 6 and 7 of the PSE, in particular tungsten oxide, molybdenum oxide and/or a precursor thereof, which are the active components and are deposited on at least one inorganic carrier. The most preferred metal oxide is tungsten oxide.

Preferably, the at least one inorganic carrier is selected from a group comprising silica, alumina, silica-alumina or aluminium phosphate. The inorganic carrier can contain at least about 0.1 wt % and up to 40 wt % of the active components. Amounts between 1 to 30 wt % are preferred, whereby amounts between 2 to 15 wt % are mostly preferred.

The metathesis catalyst may further comprise at least one oxide of a metal of group I of the PSE or a precursor thereof as for instance comprising oxides, hydroxides, carbonates, bicarbonates, nitrates, acetates of sodium or potassium or mixtures thereof. Especially preferred are the hydroxides of sodium and potassium. Said compounds have the function to modify the surface acidity of the silica in the metathesis catalyst. The amount of these modifying compounds can be between 0.01 and 10 wt %, preferably between 0.1 and 1.0 wt % with respect to the metathesis catalyst.

It is known that the bulk concentration of e.g. sodium in silica has to be lower than 500 ppm (WO 2005/049534).

It is further possible that the metathesis catalyst undergoes a pre-treatment with at least one oxide of a metal of group 1 of the PSE or a precursor thereof. For example it is preferred if silica supported tungsten oxide is used as metathesis catalyst it undergoes a pre-treatment with potassium hydroxide.

The BET surface area of the metathesis catalyst is at least >10 m$^2$/g, preferably at least >50 m$^2$/g and mostly preferably at least ≥100 m$^2$/g.

The particle size of the metathesis catalyst depends on the reactor size. When applied as powder like for instance in lab size reactors, the typical particle size of the metathesis catalyst is between 0.3-0.7 mm. When used in larger reactors like for instance technical reactors the particle size is in the range between 1 and 10 mm, preferably between 1 and 8 mm, most preferably between 1 and 5 mm.

In another preferred embodiment said second catalyst component for double bound isomerisation of the main bed composition comprises group 2 metal oxides, in particular magnesium oxide, calcium oxide, barium oxide or strontium oxide.

The isomerisation catalyst may also be activated for instance by heating in a flow stream of an oxygen-containing gas for about 1 to 30 hours at about 250° C. to 800° C. After calcination the isomerisation catalyst may be treated under reducing conditions as for instance with a reducing gas as hydrogen or carbon monoxide (U.S. Pat. No. 4,575,575; U.S. Pat. No. 3,546,313).

The main catalyst bed can then be prepared by admixture of the isomerisation catalyst and the metathesis catalyst. The catalysts are preferably mixed in form of powders, pellets or extrudates.

The amount of the isomerisation catalyst is preferably in excess of the amount of the metathesis catalyst. However, the isomerisation catalyst can also be used in lower amounts. In an embodiment the main catalyst bed comprises the at least one isomerisation catalyst component and the at least one metathesis catalyst component in a ratio between 5:1 and 1:1, preferably in a ratio 4:1 and 2:1, most preferably in a ratio of 3:1.

It is furthermore desirable if at least one catalyst pre-bed comprising at least one compound selected from the group of alkaline earth oxides is arranged upstream of the at least one main catalyst bed. The catalyst pre-bed may be arranged on top of the main catalyst bed, for example in direct physical contact with the top layer of the catalyst bed. It is also conceivable that the catalyst pre-bed is arranged spatially separated from the main catalyst bed in a separate reactor (pre-reactor). In this case the pre-reactor with the catalyst pre-bed and the synthesis reactor with the main catalyst bed are arranged sequentially. When using a catalyst pre-bed the olefin stream contacts at first the catalyst pre-bed, where a partial isomerisation of 1-butene to 2-butene may occur, and subsequently enters the main catalyst bed for further isomerisation and metathesis reaction.

The mass ratio of the catalyst pre-bed and the main catalyst bed comprising metathesis catalyst and isomerisation catalyst is between is between 1:10 and 3:1, preferably between 1:6 and 2:1, most preferably between 1:4 and 1:2. In a most preferred embodiment the mass ratio of pre-bed to main bed catalyst is 1:1. The mass ratio of catalyst pre-bed and main catalyst bed may be thus for instance 2.5:1, 2:1, 1:1 or 1:2. The specific mass ratio of catalyst pre-bed and main catalyst bed can have an impact on the catalytic performance. For instance, the cycle time and production time may increase with rising ratio of catalyst pre-bed to main catalyst bed. An optimal ratio has been found for instance in a range between 1:2 and 2.5:1.

The pre-reactor and synthesis reactor are preferably fixed-bed reactors. Basic types of catalytic fixed-bed reactors are the adiabatic fixed-bed reactor and the isothermal fixed-bed reactor. The adiabatic fixed-bed reactor is preferred for technical processes. Pre-bed and main-bed are usually provided in the fixed-bed reactor in form of random packings of powders, pellets or extrudates, for instance of catalytic pellets.

In an embodiment the at least one pre-reactor and the at least one synthesis reactor have in each case a length to diameter ratio (l/d ratio) between 1 and 15, preferably between 1 and 10, most preferably between 1 and 5, even more preferably between 1.5 and 3.5.

However, it is also conceivable and possible that the pre-bed reactor and the main bed reactor are of different volumes. It is for instance of an advantage if the pre-bed reactor is of a smaller volume than the main bed reactor. The volume ratio (V/V) of pre-bed and main-bed reactor may be 0.05-1.0, preferably 0.1-0.8, more preferably 0.2-0.5, most preferably 0.2-0.3.

It is furthermore that the pre-bed reactor and the main-bed reactor are operated at different temperatures. For instance, the operational temperature T1 of the pre-bed reactor may be in a range between 150° C. and 300° C., preferably 200° C. and 300° C., most preferably between 220° C. and 280° C., outmost preferably between 240° C. and 260° C., in particular at 250° C., and the operational temperature T2 of the main-bed reactor may be in a range between 250° C. and 350° C., preferably between 270° C. and 330° C., most preferably between 290° C. and 310° C., mostly preferred at 300° C.

In another variant of the present process the compound used as pre-bed and/or the isomerisation catalyst in the main bed can undergo a thermal pre-treatment before use, wherein the pre-treatment comprises at least one cycle of successive treatment in an oxidizing and reducing atmosphere. For example, the pre-treatment cycle may comprise the steps of:
a) heating the compound in an inert gas atmosphere to a temperature between 300° C. and 500° C., preferably 400° C.; b) treating the compound in an oxygen containing atmosphere at temperatures between 400° C. and 600° C., preferably between 500° C. and 550° C., most preferably at 525° C.; possibly followed by flushing with nitrogen c) treating the compound in a hydrogen containing atmosphere at temperatures between 300° C. and 500° C., preferably at 400° C.; d) flushing the compound with an inert gas at temperatures between 400° C. and 600° C., preferably between 400° C. and 550° C., most preferably at 550° C.; and e) subsequent cooling down the compound, preferably to a temperature between 200 and 350° C., most preferably to 300° C.

Thus, in a further embodiment of the present process a pre-aged isomerisation catalyst such as pre-aged MgO can be used in the main catalyst bed as isomerisation catalyst while a pre-aged alkaline earth oxide e.g. pre-aged or pre-treated MgO is used simultaneously as catalyst pre-bed. The isomerisation catalyst of the main catalyst bed and the alkaline earth oxide of the catalyst pre-bed were preferably pre-treated in the same manner and under the same conditions as described above.

In another embodiment of the present process the main catalyst bed comprising metathesis catalyst and isomerisation catalyst and the catalyst pre-bed comprising pure isomerisation catalyst are activated before the actual metathesis reaction of olefins.

Such an activation process may comprise the steps of:
a) heating the catalyst bed in an inert gas atmosphere to a temperature between 300° C. and 500° C., preferably 400° C.;
b) treating the catalyst bed in an oxygen containing atmosphere e.g. such as air at temperatures between 400° C. and 600° C., preferably 400° C. and 550° C.; most preferably 525;
c) treating the catalyst bed in a hydrogen containing atmosphere at temperatures between 300° C. and 500° C., preferably at 400° C.,
d) heating the catalyst bed in an inert gas atmosphere at temperatures between 400° C. and 600° C., preferably 400° C. and 550° C.; and
e) subsequent cooling down the catalyst bed in an inert gas atmosphere.

In a typical embodiment of the activation procedure the catalyst bed is heated starting at room temperature for example at a heating rate of 5 K/min until an end temperature e.g. of about 400° C. is reached and is held at this temperature for about 2 hours.

In the next step the catalyst bed is treated in air, wherein the start temperature may be 400° C. and the end temperature may be 525° C. The heating rate is for example about 5 K/min during the oxidation. The holding time at the end temperature may be about 2 hours.

Subsequently the catalyst bed treated in the oxidizing atmosphere is cooled down in an inert gas atmosphere, such as nitrogen gas atmosphere from the oxidation temperature of e.g. 525° C. to 400° C. (for example with a of cooling rate 2 K/min) and is held at the latter temperature for about 0.5 h. The treatment of the catalyst bed under reducing conditions is carried out in a gas mixture of nitrogen and hydrogen with a molar ratio of about 80:20, preferably 70:30 at e.g. about 400° C. for about 0.5-1 h, preferably for about 0.5 h. Following the reduction the catalyst is now purged with nitrogen at 400° C. for about 0.5-1 h, preferably for about 0.5 h.

The catalyst bed treatment under reducing conditions is followed by a heating (desorption) step in an inert gas atmosphere, e.g. nitrogen gas. The desorption step may last 10-20 h, preferably 14-16 h. During this time the temperature may be raised from about 400° C. to about 550° C. for example with a heating rate of about 5 K/min. Finally, the catalyst bed is cooled down in an inert gas atmosphere, e.g. nitrogen gas.

It is to be understood that the reaction parameter for reduction and activation such as the heating and/or cooling rates as provided depend on the overall size of the catalyst bed and the reactor size. In particular said heating and/or cooling rates have to be adapted, accordingly. For instance, in case of an upscaling of the reactor size reduced heating rates may be practically in order to ensure a homogenous temperature increase throughout the catalyst bed.

After each metathesis cycle the present catalyst bed undergoes a regeneration cycle.

The regeneration cycle includes heating in an oxygen gas atmosphere at temperatures between 400° C. and 600° C., preferably between 420° C. and 550° C. In a preferred embodiment the catalyst bed is heated at 420° C. in an oxidizing atmosphere with 1-2 vol % oxygen, e.g. 1 vol % oxygen in nitrogen, followed by increasing the oxygen concentration to 3 to 4 vol %, preferably 3 vol % with a simultaneous temperature rise to 480° C. and a further increase of oxygen concentration to 5 to 7 vol % oxygen, preferably 6 vol % oxygen, with a simultaneous temperature rise to 525° C. Subsequently, the catalyst bed is subjected to an air atmosphere at temperatures between 450° C. and 550° C., preferably 525° C., for 1 to 5 h, preferably 3 h, followed by cooling down to a temperature between 300° C. and 400° C., preferably to 400° C., in an inert gas atmosphere, such as nitrogen atmosphere.

In a preferred embodiment the regeneration cycle is followed by an activation cycle before starting the next metathesis cycle. This activation/regeneration/metathesis cycle can be repeated several times, for example at least twice, preferably at least five times, more preferably at least nine times.

The present metathesis reaction is preferably performed at a weight hourly space velocity (WHSV) in the range between 1 and 100 $h^{-1}$, preferably between 1 and 50 $h^{-1}$, more preferably between 1 and 10 $h^{-1}$ (the WHSV values are referring to the main catalyst bed and the fed 2-buten).

The metathesis catalyst is very sensitive to impurities in the feed stream. Such feed poisons are, for example, strong polar or protic compounds such as N—, O—, S— and halogen comprising compounds or carbon oxide derivatives. Typical examples are water, alcohols, ethers, ketones, aldehydes, acids, carbon dioxide, carbon monoxide, carbon oxide sulfide and the like. The consequences are reduced catalyst activity and shortened cycle times. Therefore the feed stream must be purified by passing it through suitable adsorbents before feeding to the reactor.

The effluent from the metathesis reactor can be sent to a separation system for separating the product(s) from unreacted feed components. For instance, the products of the separation system may include ethene, propene, and minor amounts of C4- and C5-compounds. The propene separated from the reaction stream is characterised by a high purity. The ethene and C4 olefins may be recycled back to the metathesis reactor or to a pre-treatment stage.

The present process is carried out in a metathesis reactor as described above. The metathesis reactor may be connected upstream with at least one evaporator for concentrating the olefin gas stream. Such an evaporator may be operated at temperatures between 150 and 250° C., preferably between 200 and 220° C. When using a C2- and a C4-olefin as starting material, the C4-olefin may be fed to the evaporator at the bottom thereof and the C2-olefin may be fed to the evaporator at the middle thereof. In addition, hydrogen is fed to the evaporator.

BRIEF DESCRIPTION OF THE DRAWINGS

The present invention is further explained in more detail by the means of the following examples with reference to the Figures. It shows.

DETAILED DESCRIPTION OF THE INVENTION

Example 1: A First Standard Reactor Configuration without Hydrogen (Comparative Example)

Catalytic tests were performed in a tubular (4 mm i.d.) continuous-flow fixed-bed reactor made of quartz at 1.4 bar and 300° C. using a $C_2H_4$:trans-2-$C_4H_8$:$N_2$=64.3:25.7:10 feed. $C_2H_4$ (Linde, purity>99.95%), trans-2-$C_4H_8$ (Linde, purity>99.0%) were extra purified with molsieve 3A, while "oxysorb" (Resteck) and molsieve 3A were applied for purifying $N_2$ (Air Liquide, purity>99.999%). The main catalyst is a physical mixture of MgO (0.3-0.7 mm) and $WO_x$/$SiO_2$ (0.3-0.7 mm) with a weight ratio of 3.0. The MgO (0.3-0.7 mm) was additionally used as a pre-bed arranged upstream. Both beds were placed within the isothermal zone of the reactor. The weight hourly space velocity (WHSV) was of 1.9 $h^{-1}$ related to trans-2-$C_4H_8$ and the main catalyst.

Before catalytic testing, the following pre-treatment was performed. The reactor was heated in a flow of pure nitrogen up to 400° C. with a heating rate of 5 K·$min^{-1}$. The temperature was held constant for 2 h. Hereafter, an air flow was fed to the reactor followed by temperature rising to 525° C. with a heating rate of 5 K·$min^{-1}$. After 2 hours in this flow at the final temperature, the reactor was cooled to 400° C. (2 K·$min^{-1}$) in a flow of pure nitrogen. The temperature was held constant for 0.5 h followed by feeding an $H_2$:$N_2$=30:70 (mol/mol) gas mixture for 0.5 h. Then, the reactor was flushed with a flow of pure nitrogen and heated in the same flow up to 550° C. with a heating rate of 5 K·$min^{-1}$. The temperature was held constant for 16 h. Finally, the reactor was cooled down to 300° C., where the metathesis reaction was studied.

Figure 1:
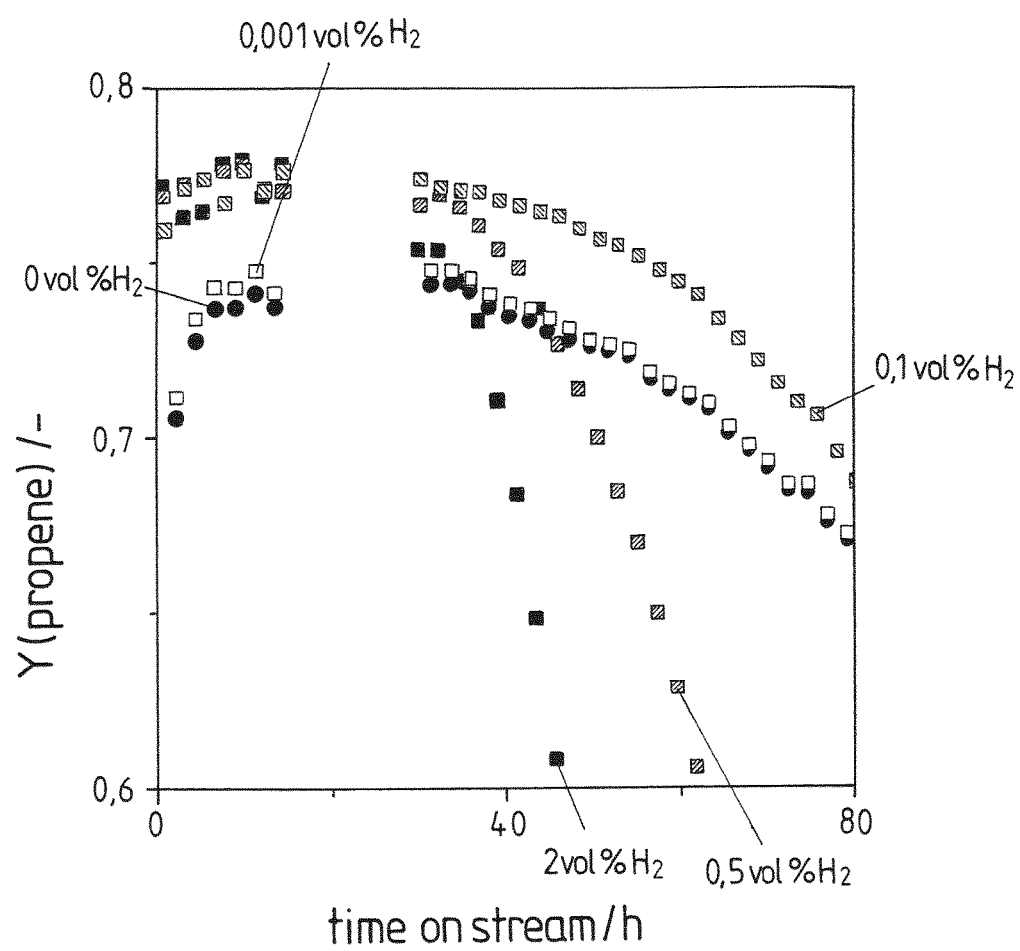
FIG. 1 a diagram illustrating the initial time on stream yield of propene obtained by ethen-2-butene metathesis co-fed with hydrogen at different concentrations.

FIG. 1 shows the yield of propene (equation 1) as a function of time on stream.

$$Y_{C_3H_6} = S_{C_3H_6} \times H_{n\text{-}butenes} \quad (1),$$

where $S_{C_3H_6}$ is propene selectivity calculated according to $$S_{C_3H_6} = \frac{m^{outlet}_{C_3H_6}}{m^{outlet}_{C_3H_6} + \sum m^{outlet}_{C_5} + \sum m^{outlet}_{C_6}}, \quad (2)$$

where $m^{outlet}$ is mass flow of $C_3H_6$, $C_5$ and $C_6$ olefins, respectively $X_{n\text{-}butenes}$ is conversion of n-butenes, calculated according to $$X_{n\text{-}butenes} = \left(1 - \frac{X^{outlet}_{t\text{-}2\text{-}C_4H_8} + X^{outlet}_{1\text{-}C_4H_8} + X^{outlet}_{cis\text{-}2\text{-}C_4H_8}}{X^{inlet}_{t\text{-}2\text{-}C_4H_8}}\right) \quad (3)$$

where $x_i^{inlet}$ and $x_i^{outlet}$ represent mole fractions of 1- or 2-butenes at the reactor inlet and outlet, respectively.

Example 2: First Standard Reactor Configuration with 0.1 Vol % Hydrogen (Inventive Example)

The test was carried out as described in Example 1 but using the standard feed additionally containing 0.1 vol % $H_2$.

Example 3: Second Standard Reactor Configuration and Technical Conditions Without Hydrogen (Comparative Example)

A liquid technical C4 stream containing 82 wt % 2-butene, 1 wt % 1-butene, 1 wt % iso-butene and 16 wt % n-butane was fed over a treatment tower filled in flow direction with 90 vol. % Selexsorb CD and 10 vol. % Selexsorb COS into a metering tank. The tank is connected over a cooler with a HPLC pump. The cooler was kept at a temperature of 3° C. A C4 flow of 3.6 g/min was fed by means of the pump to an evaporator which was operated at 215° C. The evaporator has two inlets, one at the bottom and a second in the middle of the tube (volume 450 ml). The C4 entered the evaporator at the bottom and was evaporated. In a second stream 5.73 Nl/min ethene was fed by means of a flow controller and entered the evaporator at the middle inlet. The mixed feed passed a static mixer and entered the metathesis reactor at the top flange, past the catalyst bed and left the reactor at the bottom. The inlet and outlet feed composition was analyzed with an Agilent 7890 gas chromatograph using a HP Al/S column.

The reactor had an internal diameter of 38 mm and a length of 900 mm. For the preparation of the catalyst bed MgO and $WO_3$—$SiO_2$ pellets with a size of 2-4 mm were physically mixed in a mass ratio of 3:1. 113.2 g of the mixture was placed in the reactor as main-bed. Upstream to the main-bed 28.3 g MgO were introduced as pre-bed. The catalyst beds were placed in the middle of the reactor in an isothermal zone and the space between reactor bottom and catalyst bed as well as that above the bed was filled with alumina bed support balls with a size of ¼ inch. The temperature of the bed was adjusted to 280° C. and was kept constant over the whole time on stream. The reaction pressure was 25 bar, the E/B mole ratio 4.0 and the WHSV was 1.6 h$^{-1}$.

Before catalytic testing, the following pre-treatment was performed. The reactor was heated in a flow of pure nitrogen up to 300° C. with heating rate of 0.2 K·min$^{-1}$ at a pressure of 3 bar. Hereafter, an oxygen stream was added to adjust an oxygen content of 5 vol %. The temperature was kept constant for 2 hours. After that the temperature was raised to 400° C. with a heating rate of 0.2 K·min$^{-1}$ and the oxygen content was increased to 10 vol %. The temperature was kept constant for 2 further hours. After treatment at 400° C. the temperature was raised to 525° C. with the above mentioned heating rate. Pure synthetic air was used for the final oxidation step.

After 2 hours in this flow at the final temperature, the reactor was cooled to 400° C. (0.7 K·min$^{-1}$) in a flow of pure nitrogen. The temperature was held constant for 0.5 h followed by feeding a hydrogen flow of 0.9 Nl/h for 0.5 h. Then, the reactor was flushed with a flow of pure nitrogen and heated in the same flow up to 550° C. with a heating rate of 0.2 K·min$^{-1}$. The temperature was held constant for 16 h. Finally, the reactor was cooled down to 280° C., where the metathesis reaction was started.

The conversion increased during the first 116 hours from 81% to a maximum of 87%, was constant for further 184 hours and decreased afterwards. The conversion after 400 hours was 84%.

Example 4: Second Standard Reactor Configuration Technical Conditions with 0.2 Vol % Hydrogen in the Feed (Inventive Example)

The experiment was carried out in the same way as described in example 3. In addition to the olefin feed 0.2 vol % hydrogen were fed to the evaporator.

The conversion increased after 2 hours to 88% and stayed constant over a time of 400 hours.

Example 5: First Standard Reactor Configuration with 0.5 Volume % Hydrogen (Comparative Example)

The test was carried out as described in Example 1 but using the standard feed additionally containing 0.5 vol % H$_2$.

Example 6: First Standard Reactor Configuration with 2 Vol % Hydrogen (Comparative Example)

The test was carried out as described in Example 1 but using the standard feed additionally containing 2 volume % H$_2$.

Example 7: First Standard Reactor Configuration with 0.001 Vol. % Hydrogen

The test was carried out as described in Example 1 but using the standard feed additionally containing 0.001 vol. % H$_2$.

The results of the conversion using the first standard reactor configuration with different amounts of hydrogen are depicted in the diagram of FIG. 1.

FIG. 1 shows the time on-stream yield of propene in ethylene-2-butene metathesis to propene over standard catalyst at 300° C. a C$_2$H$_4$:trans-2-C$_4$H$_8$:N$_2$:H$_2$=64.3:25.7:(10-x):x feed at a reaction pressure of 1.2 bar in a time on stream range of up to 80 h.

FIG. 1 depicts the time on stream yield using different concentrations of co-fed hydrogen, namely 0 vol % H$_2$, 0.001 vol % H$_2$, 0.1 vol % H$_2$, 0.5 vol % H$_2$ and 2 vol % H$_2$.

The results clearly indicate that the total amount of propene in the conversion range above 60% is higher at a hydrogen concentration about 0.1 Vol %. In particular the results show that the initial time-on-stream yield of propene (that means within the first 80 hours reaction time) is increased when co-feeding hydrogen compared to no-co-feeding of hydrogen.

In addition, the results also show that the time-on-stream yield is further influenced by the amount of hydrogen co-fed. Co-feeding 0.1 vol % hydrogen improved the propene yield over an extended period of time (up to 80 hours) while the propene yield using a concentration of 0.5 vol % hydrogen dropped rapidly after about 40 h time on stream and was even worse compared to the olefin fed without hydrogen. Co-feeding only 0.001 vol % hydrogen on the other hand showed no influence on the time-on-stream yield in respect to the standard condition without hydrogen.

The massive beneficial influence of small amounts of hydrogen on the initial time on stream yield was in view of the prior art surprising and not to be expected.

Example 8: First Standard Reactor Configuration Technical Conditions with 0.2 vol % Hydrogen in the Feed (Inventive Example)

The test was carried out as described in Example 1 but using the standard feed additionally containing 0.2 vol % H$_2$.

Example 9: First Standard Reactor Configuration with 0.3 Volume % Hydrogen (Comparative Example)

The test was carried out as described in Example 1 but using the standard feed additionally containing 0.3 vol % H$_2$.

Figure 2:
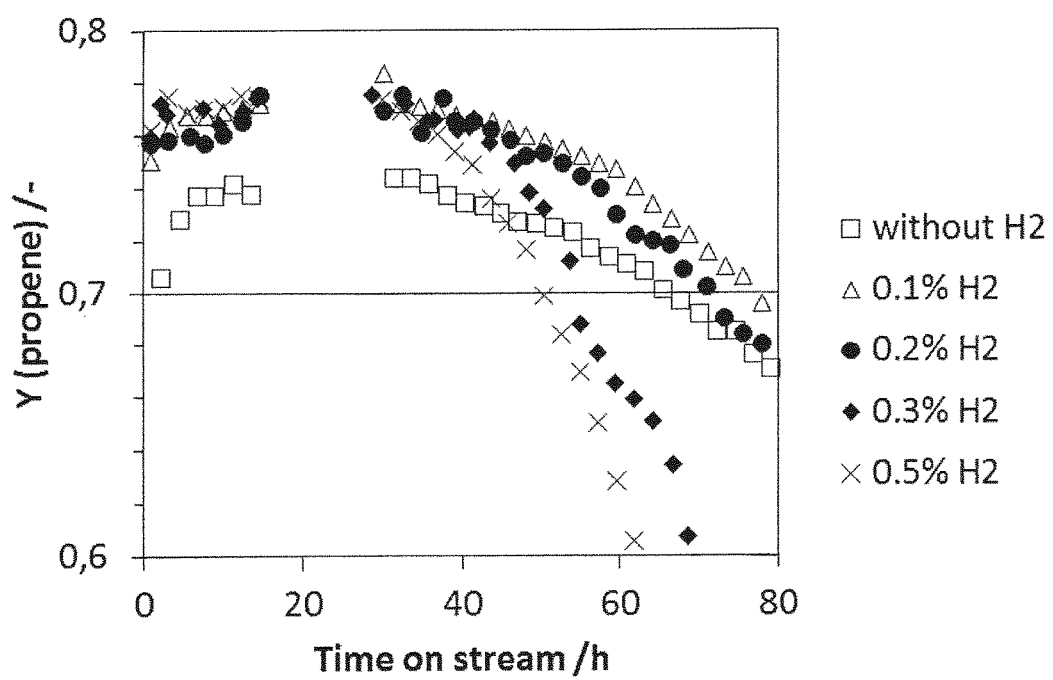
FIG. 2 a further diagram illustrating the initial time on stream yield of propene obtained by ethen-2-butene metathesis co-fed with hydrogen at different concentrations.

The results of the conversion of example 8 and 9 using the first standard reactor configuration with different amounts of hydrogen are depicted in the diagram of FIG. 2.

FIG. 2 shows the time on-stream yield of propene in ethylene-2-butene metathesis to propene over standard catalyst at 300° C. a C$_2$H$_4$:trans-2-C$_4$H$_8$:N$_2$:H$_2$=64.3:25.7:(10-x):x feed at a reaction pressure of 1.2 bar in a time on stream range of up to 80 h.

FIG. 2 depicts the time on stream yield using different concentrations of co-fed hydrogen, namely 0 vol % H$_2$, 0.1 vol % H$_2$, 0.2 vol % H$_2$, 0.3 vol % H$_2$ and 0.5 vol % H$_2$.

The results clearly indicate that the total amount of propene in the conversion range above 60% is higher at a hydrogen concentration about 0.1 and 0.2 Vol %. In particular the results show that the initial time-on-stream yield of propene (that means within the first 80 hours reaction time) is increased when co-feeding hydrogen compared to no-co-feeding of hydrogen.

In addition, the results also show that the time-on-stream yield is further influenced by the amount of hydrogen co-fed. Co-feeding up to 0.2 vol % hydrogen improved the propene yield over an extended period of time (up to 80 hours) while the propene yield using a concentration of >/=0.3 vol % hydrogen dropped rapidly after about 45 h time on stream and was even worse compared to the olefin fed without hydrogen.

The invention claimed is:

1. A process for obtaining an olefin by metathesis comprising
feeding at least one stream comprising at least one olefin as starting material and hydrogen gas in a concentration range between 0.01 vol % and 0.2 vol % in respect to the total gas amount in the stream to at least one reactor comprising at least one main catalyst bed, the at least one main catalyst bed comprising
a) at least one first catalyst component comprising a metathesis catalyst, and
b) at least one second catalyst component comprising a catalyst for double bond isomerisation, whereby the first and second catalyst are physically mixed with each other, and
conducting a metathesis process in the at least one reactor at a pressure between 0.1 MPa and 3.0 MPa and at a temperature between 250° C. and 300° C.

2. The process according to claim 1, wherein the hydrogen gas is co-fed in a concentration range between 0.05 vol % and 0.2 vol %, in respect to the total gas amount in the stream.

3. The process according to claim 1, wherein the reaction pressure is between 0.12 MPa and 2.5 MPa.

4. The process according to claim 1, wherein the reaction temperature is between 270° C. and 300° C.

5. The process according to claim 1, wherein at least two olefins are fed as starting material.

6. The process according to claim 5, wherein a first of the at least two olefins used as starting material comprises at least two carbon atoms (C2-compound) and a second of the at least two olefins used as starting material comprises at least four carbon atoms (C4-compound).

7. The process according to claim 6, wherein the ratio of the C2-compound and the C4-compound is 20:1.

8. The process according to claim 1, wherein the main catalyst bed comprises the at least isomerisation catalyst component and the at least one metathesis catalyst component in a ratio between 5:1 and 1:1.

9. The process according to claim 1, wherein the metathesis catalyst comprises oxides of metals of the 6th and 7th group of the Periodic Table of the Elements deposited on at least one inorganic carrier.

10. The process according to claim 1, wherein said second catalyst component for double bond isomerisation of the main catalyst bed comprises Group 2 metal oxides.

11. The process according to claim 1, wherein at least one catalyst pre-bed comprising at least one compound selected from the group of alkaline earth oxides is arranged upstream of the at least one main catalyst bed.

12. The process according to claim 11, wherein the mass ratio of the catalyst in the pre-bed and the catalyst mixture of metathesis catalyst and isomerisation catalyst in the main catalyst bed is between 1:10 and 3:1.

13. The process according to claim 11, wherein said compound comprises magnesium oxide, calcium oxide, strontium oxide, barium oxide or a mixture thereof.

14. The process according to claim 1, wherein the isomerisation catalyst of the main catalyst bed and/or the catalyst pre-bed are subjected to a pre-treatment before use, wherein the pre-treatment comprises at least one cycle comprising a successive treatment in an oxidizing and reducing atmosphere.

15. The process according to claim 1, wherein the complete catalyst bed comprising the at least one main catalyst bed and the at least one catalyst pre-bed is activated in a process comprising the steps of
a) heating the catalyst bed in an inert gas atmosphere to a temperature between 300° C. and 500° C.;
b) treating the catalyst bed in an oxygen containing atmosphere at temperatures between 400° C. and 600° C.;
c) treating the catalyst bed in a hydrogen containing atmosphere at temperatures between 300° C. and 500° C.,
d) heating the catalyst bed in an inert gas atmosphere at temperatures between 400° C. and 600° C.; and
e) subsequent cooling down the catalyst in an inert gas atmosphere.

16. The process according to claim 2, wherein the hydrogen gas is co-fed in a concentration range between 0.05 vol % and 0.1 vol % in respect to the total gas amount in the stream.

17. The process according to claim 3, wherein the reaction pressure is between 1.0 MPa and 2.0 MPa.

18. The process according to claim 4, wherein the reaction temperature is between 280° C. and 300° C.

19. The process according to claim 6, wherein the C2-compound is ethene and the C4-compound is 2-butene.

20. The process according to claim 7, wherein the ratio of the C2-compound and the C4-compound is 2.5:1.

21. The process according to claim 1, wherein the reaction pressure is between 2.0 and 3.0 MPa.

* * * * *